United States Patent [19]

Ohsumi et al.

[11] Patent Number: 4,511,581
[45] Date of Patent: Apr. 16, 1985

[54] FUNGICIDAL INDANYLBENZAMIDE

[75] Inventors: Tadashi Ohsumi, Fanabashi; Satoru Inoue, Takarazuka; Kiyoto Maeda, Nishinomiya, all of Japan

[73] Assignee: Sumitomo Chemical Company, Limited, Osaka, Japan

[21] Appl. No.: 464,864

[22] Filed: Feb. 8, 1983

[30] Foreign Application Priority Data

Feb. 10, 1982 [JP] Japan .................................. 57-20321

[51] Int. Cl.³ ...................... A01N 37/18; C07C 103/76
[52] U.S. Cl. ..................................... 514/617; 564/166; 564/184; 514/619
[58] Field of Search ................ 424/324; 564/166, 184

[56] References Cited

U.S. PATENT DOCUMENTS

| | | | |
|---|---|---|---|
| 2,069,804 | 2/1937 | Heckert | 564/184 X |
| 2,965,575 | 12/1960 | Beaver et al. | 564/184 X |
| 3,721,709 | 3/1973 | Mueller et al. | 564/184 |
| 3,936,293 | 2/1976 | Rathgeb et al. | 71/118 |
| 3,985,804 | 10/1976 | Chiyomaru et al. | 564/184 |
| 4,093,743 | 6/1978 | Yabutani et al. | 424/324 |
| 4,123,554 | 10/1978 | Kawada et al. | 564/184 X |

FOREIGN PATENT DOCUMENTS

EP86111 8/1983 European Pat. Off. ............ 564/184

*Primary Examiner*—Thomas A. Waltz
*Attorney, Agent, or Firm*—Cushman, Darby & Cushman

[57] ABSTRACT

A fungicidal indanylbenzamide derivative of the formula:

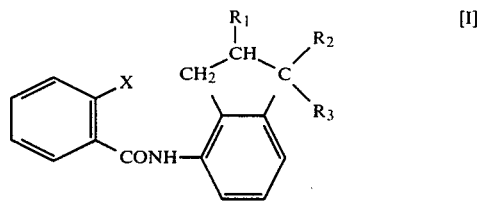

wherein X is a lower alkyl, nitro, or trifluoromethyl group or a halogen atom, and $R_1$, $R_2$ and $R_3$, which are same or different, each represents a hydrogen atom or a lower alkyl group.

10 Claims, No Drawings

FUNGICIDAL INDANYLBENZAMIDE

The present invention relates to a fungicidal indanylbenzamide derivative. More particularly, it pertains to an indanylbenzamide derivative of the formula:

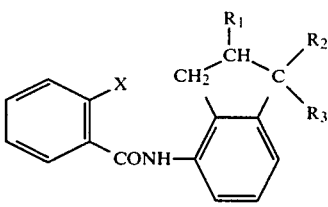

wherein X is a lower alkyl, nitro, or trifluoromethyl group or a halogen atom, and $R_1$, $R_2$ and $R_3$, which are same or different, each represents a hydrogen atom or a lower alkyl group, to its fungicidal use and compositions and to a process for producing them.

In the present specification, the term "lower alkyl" means an alkyl having one to three carbon atoms.

As a result of our study, we have found that the said indanylbenzamide derivatives of the formula [I] have excellent fungicidal properties.

The indanylbenzamide derivatives of the present invention can be prepared by a conventional method. More specifically, they can be prepared by reacting a benzoic acid derivative of the formula:

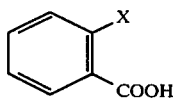

wherein X is as defined above, or its reactive derivatives with an aminoindan derivative of the formula:

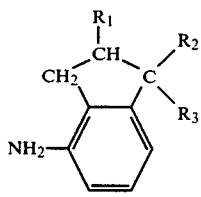

wherein $R_1$, $R_2$ and $R_3$ are as defined above.

As the reactive derivatives of the benzoic acid of the formula [II], such derivatives as acid anhydrides (including mixed acid anhydrides), acid chloride, acid bromide, or esters are used in this process. These reactive derivatives or the benzoic acid of the formula [II] are principally reacted with the aminoindan derivatives of the formula [III] in a mole ratio of approximately 1:1.

A suitable inert solvent may be used in the process. Examples of such solvents are aromatic hydrocarbons such as benzene, toluene, or xylene, halogenated hydrocarbons such as chlorobenzene, chloroform, dichloromethane, or carbon tetrachloride, ethers such as diisopropyl ether, tetrahydrofuran, or dioxan, ketones such as methyl ethyl ketone or acetone, esters such as ethyl acetate, nitrile such as acetonitrile, tertiary amines such as triethylamine or pyridine, dimethylsulfoxide or dimethylformamide or a mixture thereof.

When the benzoic acid derivatives of the formula [II] are used in the form of free acid, the process is carried out under the dehydrating conditions. It may be conducted by heating the reactants at a relatively high temperature, preferably from 150° C. to 250° C. It may also be conducted by reacting the benzoic acid of the formula [II] with the compound of the formula [III] in the presence of a dehydrating agent (e.g., dicyclohexylcarbodiimide, phosphorus tetrachloride). In this case, the reaction may be conducted at a relatively low temperature ranging from 0° C. to the boiling point of the used solvent, preferably from room temperature to 80° C. The preferable amount of the dehydrating agent may be one to two moles per one mole of the benzoic acid.

When the acid anhydrides, acid chloride or acid bromide of the benzoic acid of the formula [II] is used, it is preferable to carry out the reaction in the presence of an acid acceptor. Examples of suitable acid acceptor are organic or inorganic bases such as sodium hydroxide, potassium hydroxide, pyridine, N-methylmorpholine, triethylamine and the like. These acid acceptors are not necessarily used in excessive amounts, but it is preferable to add one or more moles, preferably one to one and a half mole per one mole of the used compound [II]. Although the use of a solvent is not essential, a good result may be obtained when the reaction is carried out in a solvent chosen from the above said inert solvents or water or a mixture thereof. The reaction temperature is not particularly limited, but the reaction is usually conducted at a temperature in a range from 0° C. to a boiling point of the used solvent, preferably from 0° C. to 80° C.

When the ester of the benzoic acid of the formula [II] (e.g., lower alkyl esters) is used, the reaction may be carried out by simply heating the reaction mixture at a relatively high temperature, preferably from 100° C. to 250° C. The reaction may also be carried out in the presence of a catalyst such as sodium ethoxide. The amount of the catalyst may be 0.1 to 1.5 mole per 1 mole of the used ester. In this case, the reaction temperature may be about a boiling point of the used solvent, preferably 80° C. to 150° C.

After the reaction has been completed, the product is isolated from the reaction mixture by a conventional method. For example, the catalyst or other agents used are removed by washing with water or filtration, the mixture is extracted with a solvent and the extract is washed with water and evaporated to give the crude product, which may further be purified by recrystallization from benzene, toluene, methanol, ethanol, diisopropyl ether, hexane, chloroform, and the like.

The compound of the formula [II] is readily prepared by a known method [Hans Hoyer Journal für praktische Chemie 139, 242 (1934); ibid., 139, 94 (1934); M. G. J. Beets etc., Rec. Trav. Chim. Pays-Bas 77, 860 (1958); E. Giovannini et al., Helvetica Chimica Acta 49, 561 (1966)].

The following Synthesis Examples are given to illustrate the present invention more precisely, but the present invention is not limited only to them.

Synthesis Example 1

A solution of 0.81 g of o-methylbenzoyl chloride (5.25 m mol) in 3 ml of tetrahydrofuran is added dropwise to a solution of 0.81 g of 1,1-dimethyl-4-aminoindan (5.00 m mol) and 0.61 g of triethylamine (6.00 m mol) in 10 ml of tetrahydrofuran, while maintaining the reaction mixture at 0° C. by ice-cooling. Then, reaction mixture is stirred over night at room temperature, and water and ethyl acetate are added to the mixture. The organic layer is washed with 5% hydrochloric acid and water and dried over anhydrous sodium sulfate. After the solvent is removed by distillation, the residue is dried to give 1.31 g of N-(1,1-dimethyl-4-indanyl)-o-methylbenzamide (yield: 93.9%).

SYNTHESIS EXAMPLE 2

A mixture of 2.0 g of ethyl o-methylbenzoate (12.2 m mol), 1.62 g of 4-aminoindan (12.2 m mol), 0.72 g of $CH_3ONa$ and 30 ml of benzene is stirred for 10 hours under reflux. After ice-cooling, the mixture is added to dilute hydrochloric acid and extracted with ethyl acetate. The organic layer is washed with water and concentrated. The resulting crystals are washed with n-hexane to give 2.0 g of N-4-indanyl-o-methylbenzamide (yield: 65.4%).

SYNTHESIS EXAMPLE 3

A solution of 2.06 g of dicyclohexylcarbodiimide (10.0 m mol) in 5 ml of toluene is added to a mixture of 1.90 g of o-trifluoromethylbenzoic acid and 20 ml of toluene under ice-cooling with stirring. After stirring for another one hour, a solution of 1.47 g of 1-methyl-4-aminoindan (10.0 m mol) in 5 ml of toluene is added to the mixture. The reaction mixture is warmed to room temperature and then refluxed for 10 hours. The dicyclohexylurea formed is removed by filtration from the mixture, and the filtrate is then concentrated. The residue is purified by column chromatography on silica gel to give 2.10 g of N-(1-methyl-4-indanyl)-o-trifluoromethylbenzamide (yield: 65.8%).

The followings are examples of the indanylbenzamide derivatives provided by the present invention:

TABLE 1

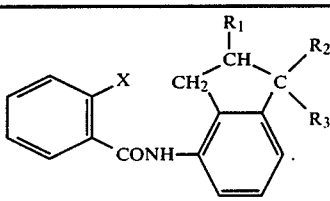

| Compound No.* | X | $R_1$ | $R_2$ | $R_3$ | Physical Constant |
|---|---|---|---|---|---|
| (1) | $CH_3$ | H | $CH_3$ | $CH_3$ | mp 126.0° C. |
| (2) | I | H | $CH_3$ | $CH_3$ | mp 155.1° C. |
| (3) | Cl | H | $CH_3$ | $CH_3$ | mp 140.4° C. |
| (4) | $NO_2$ | H | $CH_3$ | $CH_3$ | mp 212.5° C. |
| (5) | $CF_3$ | H | $CH_3$ | $CH_3$ | mp 148.7° C. |
| (6) | $CH_3$ | $CH_3$ | H | H | mp 144.9° C. |
| (7) | I | $CH_3$ | H | H | mp 201.1° C. |
| (8) | Cl | $CH_3$ | H | H | mp 137.0° C. |
| (9) | $CF_3$ | $CH_3$ | H | H | mp 173.4° C. |
| (10) | $CH_3$ | H | $CH_3$ | H | mp 140.9° C. |
| (11) | I | H | $CH_3$ | H | mp 180.8° C. |
| (12) | $CF_3$ | H | $CH_3$ | H | mp 152.6° C. |
| (13) | $CH_3$ | H | $-CH(CH_3)_2$ | H | mp 110.1° C. |
| (14) | Cl | H | $-CH(CH_3)_2$ | H | mp 95.7° C. |
| (15) | $CH_3$ | H | H | H | mp 158.6° C. |
| (16) | $CH_3$ | H | $CH_3$ | $CH_2CH_3$ | $n_D^{25.0}$ 1.5577 |

*The same Compound Nos. are used throughout the specification.

The indanylbenzamide derivatives of the present invention are fungicidally effective against various plant pathogenic fungi, particularly those belonging to genus Rhizoctonia, Corticium, Ustilago, Tilletia, Urocystis, Gymnosporangium, Uromyces, Puccinia, Helicobasidium, Typhula, Armillaria, etc.

In controlling plant diseases caused by such fungi, the compounds of the present invention an be applied as a fungicide in such amounts as 10 to 1000 g per 10 are, preferably 50 to 500 g per 10 are at concentrations of about 0.005 to 0.5% to fields including a paddy field, fruits trees, forests, and the like. However, the amounts and concentrations of the compounds may vary depending upon, for example, kind and severity of the plant disease, kind of the formulations, place, time, way of the applications, and the like.

The following TEST EXAMPLES are given to illustrate the plant disease controlling effects of the compounds of present invention. The compounds indicated in the following Table 2 are also tested for comparison. Unless otherwise indicated, the experiment is conducted three times for each TEST EXAMPLE.

TABLE 2

| Compound No. | Formula | Remarks |
|---|---|---|
| A | o-$CH_3$-C₆H₄-CONH-C₆H₅ | German Patent Application (DT-OS) 1,907,436 |
| B | o-$CH_3$-C₆H₄-CONH-C₆H₄-$OC_3H_7(i)$ | Japanese Patent Application Publication (Kokai) No. 50-148321 |
| C | o-$CF_3$-C₆H₄-CONH-C₆H₄-$OC_3H_7(i)$ | Japanese Patent Application Publication (Kokai) No. 53-9739 |
| D | Validamycin A | Commercially available fungicide |
| E | 3-Hydroxy-5-methyl-isoxazale | |
| F | Pentachloronitrobenzene | |
| G | Triforine | |

TEST EXAMPLE 1

Rice Sheath Blight Controlling Effect—Foliar Application

Rice plants (Kinki No. 33, 6 leaves stage) are cultivated in pots (9 cm in diameter). An emulsifiable concentration of test compound prepared according to the method described in FORMULATION EXAMPLE 3 is diluted with water and applied to the plants with a spray gun so that a sufficient amount of the solution of the test compound is attached to the plants.

After 7 days from the application, sheath blight fungus (*Pellicularia sasakii*) is inoculated onto the sheaths by placing a mycelial disk (5 mm in diameter) on them. Inoculated plants were placed in an air-conditioned room maintained at 28° C. under a relative humidity of more than 95% (described as the incubation room in the following). After 3 days from the inoculation, the infected area is measured. The disease severity and disease controlling effect are calculated by the following equation.

| Lesion Index | Infected area |
|---|---|
| 0 | none |
| 1 | small spot(s) |
| 2 | less than 3 cm in length |
| 3 | 3 cm or more in length |

$$\text{Severity (\%)} = \frac{\Sigma(\text{lesion index}) \times (\text{number of sheaths})}{(\text{Number of inspected sheaths}) \times 4} \times 100$$

Then, the control value is obtained by the following equation:

$$\text{Control value (\%)} = 100 - \frac{\text{Severity in treated plot}}{\text{Severity in control plot}} \times 100$$

The results are given in the following Table 3.

TABLE 3

| Test compound | Concentration of active ingredient (ppm) | Control value (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 8 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| A | 500 | 75 |
| No treatment | — | 0 |

TEST EXAMPLE 2

The compounds are tested in the same method as in TEST EXAMPLE 1 except that the compounds are applied at a concentration of 50 ppm instead of 500 ppm. The compound D is applied at 30 ppm. The results are given in the following table 4.

TABLE 4

| Test compound | Concentration (ppm) | Control value (%) |
|---|---|---|
| (1) | 50 | 95 |
| (2) | 50 | 93 |
| (4) | 50 | 90 |
| (5) | 50 | 100 |
| (6) | 50 | 90 |
| (9) | 50 | 90 |
| (10) | 50 | 93 |
| (12) | 50 | 100 |
| (16) | 50 | 91 |
| (A) | 50 | 0 |
| (B) | 50 | 29 |
| (C) | 50 | 85 |
| (D) | 30 | 51 |
| No treatment | — | 0 |

TEST EXAMPLE 3

Rice Sheath Blight Controlling Effect—Submerged Application

Rice plants (Kinki No. 33) are grown to 7th leaf stage under flooded conditions in wagner pots. An emulsifiable concentration of test compound is diluted with water and applied to the water surface of the pots. After 14 days from the application, sheath blight fungus (*Pellicularia sasakii*) is inoculated to the water surface and incubated in an incubation room. After 7 days incubation, infected area of the plants are measured. The disease controlling effect of the test compound is calculated by the same method as of TEST EXAMPLE 1. The results are shown in the following table 5.

TABLE 5

| Compound | dosage (g/10 a) | Control value (%) |
|---|---|---|
| (2) | 250 | 100 |
| (3) | 250 | 100 |
| (5) | 250 | 100 |
| (8) | 250 | 98 |
| (9) | 250 | 100 |
| (11) | 250 | 100 |
| (12) | 250 | 100 |
| (14) | 250 | 100 |
| (16) | 250 | 100 |
| (A) | 250 | 0 |
| (B) | 250 | 13 |
| (C) | 250 | 80 |
| No treatment | — | 0 |

TEST EXAMPLE 4

Controlling Effect on Damping-Off of Cucumber

Plastic pots (8 cm in diameter) are filled with sandy soil, on which soil infected with *Rhizoctonia solani*, damping-off fungus, is uniformly placed. An emulsifiable concentration of test compound is diluted with water and poured in the pots. After 2 hours from the application, 10 seeds of cucumber (cv. kagafushinari) are sowed in each pot. After 10 days from the sowing, the plants are observed to determine the number of infected plants. The results are shown in the following table 6.

TABLE 6

| Compound | dosage (g/10a) | Rate of healthy plant (%) |
|---|---|---|
| (2) | 750 | 100 |
| (3) | 750 | 100 |
| (5) | 750 | 100 |
| (8) | 750 | 100 |
| (9) | 750 | 100 |
| (11) | 750 | 100 |
| (12) | 750 | 100 |
| (14) | 750 | 100 |
| (E) | 750 | 73.3 |
| uninfected and untreated | — | 100 |
| infected and untreated | — | 6.7 |

$$\text{The rate of healthy plants (\%)} = \frac{\text{The number of healthy plants in an infected and treated plot}}{\text{The number of plants in an uninfected and untreated plot}} \times 100$$

TEST EXAMPLE 5

Controlling Effect on Southern Blight of Kidney Bean

Plastic pots (8 cm in diameter) are filled with sandy soil. 10 ml of soil infected with *Corticium rolfsii* is placed on the surface of the soil in each pot. An emulsifiable concentration of test compound is diluted with water and poured in each pot. After two hours from the application, 10 seeds of kidney bean (cv. Honkintoki) are sowed in each pot and grown for 14 days. The plants are observed to determine the number of infected plants. The results are shown in the following table 7. The rate of healthy plants is calculated by the same method as of TEST EXAMPLE 4.

TABLE 7

| Compound | dosage (Kg/10 a) | Rate of healthy (%) |
|---|---|---|
| (2) | 1.5 | 100 |
| (3) | 1.5 | 100 |
| (5) | 1.5 | 100 |
| (8) | 1.5 | 100 |
| (9) | 1.5 | 100 |
| (11) | 1.5 | 100 |

TABLE 7-continued

| Compound | dosage (Kg/10 a) | Rate of healthy (%) |
| --- | --- | --- |
| (12) | 1.5 | 100 |
| (14) | 1.5 | 100 |
| (F) | 1.5 | 76.7 |
| uninfected and untreated | — | 100 |
| infected and untreated | — | 6.7 |

TEST EXAMPLE 6

Control Effect on Brown Rust of Wheat

Plastic pots filled with sandy loam are sowed with the seed of wheat (var. Norin No. 61) at a rate of 10 to 15 seeds per pot and cultivated for 7 days in an air-conditioned greenhouse at 18° to 23° C. to allow the young wheat seedlings to grow to the developmental stage of first foliage. The seedlings at this stage are inoculated with *Puccinia recondita* and left standing in a humidified chamber at 23° C. for 16 hours to become infected with the fungus. A diluted emulsion of the test compound is then sprayed so that a sufficient amount of the mixture is attached to the plants. The pots with seedlings are kept in a constant temperature chamber at 23° C., cultivated for 10 days under radiation from a fluorescent lamp, and the symptoms on the first leaf is observed. The foliage of each seedling are then inspected for the symptoms of disease and the severity is calculated in the following way: the appearance of the lesion on the inspected leaf is classified into 5 indices, that is, 0, 0.5, 1, 2 and 4, and the disease severity is calculated by the equation given below.

| Lesion index | Appearance of lesion |
| --- | --- |
| 0 | Neither colony nor lesion was observed. |
| 0.5 | Colony or lesion of less than 5% in area based on total leaf area was observed on the leaf surface. |
| 1 | Colony or lesion of less than 20% in area based on total leaf area was observed on the leaf surface. |
| 2 | Colony or lesion of less than 50% in area based on total leaf area was observed on leaf surface. |
| 4 | Colony or lesion of 50% or more in area based on total leaf area was observed on leaf surface. |

$$\text{Severity (\%)} = \frac{\Sigma(\text{lesion index}) \times (\text{number of leaves})}{(\text{Number of inspected leaves}) \times 4} \times 100$$

The results are given in the following Table 8.

TABLE 8

| Compound | Concentration (ppm) | Control value (%) |
| --- | --- | --- |
| (2) | 500 | 99 |
| (3) | 500 | 98 |
| (5) | 500 | 93 |
| (9) | 500 | 98 |
| (G) | 500 | 89 |
| untreated | — | 0 |

The compounds of the formula [I] may be applied as they are or in the form of preparations such an oil solutions, emulsifiable concentration, wettable powders, granules, dusts, sol-compositions and the like. In the practical usage, however, they are usually brought into a preparation form by a conventional method, for example, by admixing a compound of the formula [I] with a solid or liquid carrier or diluent. If desired, other additives such as binding and/or dispersing agent (e.g., gelatin, casein, sodium alginate, CMC, starch, gum arabic powder, lignosulfonate, bentonite, polyoxypropylene glycol ether, polyvinyl alcohol, pine oil, liquid or solid parafine), stabilizer (e.g., isopropyl phosphate, tricresyl phosphate, tall oil, epoxidized oil, surfactant, fatty acid, fatty acid ester), emulsifier (e.g., alkyl sulfonate, polyoxyethylene alkylsulfate, alkylarylsulfonate, polyethylene glycol alkyl ether, polyoxyethylene alkylaryl ether), wetting agent (e.g., dodecyl benzenesulfonate, lauryl sulfate) and the like, may be incooporated.

These preparations usually contain the compound of the formula [I] in amounts of 0.1% to 99.9%, preferably 0.2% to 80% by weight.

Examples of the solid carriers are botanical materials (e.g., tobacco stalk powder, corn stalk powder, flour, soybean powder, walnut-shell powder, saw dust, and some other plant fibers), plastic materials (e.g., polyvinyl chloride, polystyrene polyethylene, petroleum resins), mineral materials (e.g., attapulgite, kaolin clay, bentonite, acid clay, sericite, vermiculite, pyrophyllite, talc, calcite, diatomite, zeolite, pumice, silica sand, active carbon, white carbon, gypsum), fertilizers (e.g., ammonium sulfate, ammonium nitrate, urea). Examples of the liquid carriers are aliphatic hydrocarbons (e.g., kerosene, machine oil, mineral spirit, solvent naphtha), aromatic hydrocarbon (e.g., xylene, methylnaphthalene, nonylphenol), alcohols (e.g., methanol, ethanol, ethylene glycol, polyethylene glycol, polypropylene glycol), ethers (e.g., dioxane, cellosolve), ketones (e.g., methyl ethyl ketone, methyl isopropyl ketone, cyclohexanone, isophorone), halogenated hydrocarbons (e.g., dichloroethane, trichloroethane, carbon tetrachloride), esters (e.g., dioctyl phthalate, tricresyl phosphate), nitrile (e.g., acetonitrile), amides such as dimethylformamide, dimethylsulfoxide, lipids, water, and the like.

The foregoing preparations may be used as they are or they may be further diluted with water before the application. If desired, other fungicides, miticides, nematicides, insecticides, herbicides, fertilizers, soil-treating agents and the like may be incorporated in the preparations.

Some practical embodiments of the fungicidal compositions of the present invention are shown below to illustrate the present invention more precisely, but the present invention is not limited only to them.

FORMULATION EXAMPLE 1

Dust 0.2 part of the compound (1) and 98.8 parts of clay are thoroughly pulverized and mixed together to obtain a dust containing 0.2% of the compound.

FORMULATION EXAMPLE 2

Emulsifiable concentration 25 parts of the compound (2), 55 parts of xylene and 20 parts of a mixture of polyoxyethylene nonyl phenol ether, polyoxyethylene-addition compound of fatty acid, and dodecylbenzene sulfonate are mixed together to obtain an emulsifiable concentration containing 25% of the compound.

FORMULATION EXAMPLE 3

Wettable powder 80 parts of the compound (3), 5 parts of dodecylbenzenesulfonate, and 15 parts of white carbon are thoroughly pulverized and mixed together to obtain wettable powder.

FORMULATION EXAMPLE 4

Sol-composition 25 parts of the compound (5), which is pulverized to less than 5μ in the average diameter with a jet mill, 5 parts of polyoxyethylene nonylphenol ether, 5 parts of carboxymethyl cellulose, and 65 parts of water are mixed together and homogenized to give the sol-composition.

FORMULATION EXAMPLE 5

Granules 10 parts of the compound (7) are sprayed on 90 parts of bentonite having adjusted particle size of 16 to 32 mesh to allow the compound to soak into the bentonite. The thus obtained granules contain 10% of the compound as the active ingredient.

FORMULATION EXAMPLE 6

Floating type granules 10 parts of the compound (9) are sprayed on 85 parts of pumice whose average particle size is 16 to 32 mesh, to allow the compound to soak into the pumice. To the pumice, 5 parts of liquid paraffin are further sprayed to give a floating type granule containing 10% of the compound.

FORMULATION EXAMPLE 7

Coating type granules 10 parts of the compound (11) are sprayed on 77 parts of silica sand, whose particle size is 16 to 32 mesh, and then 3 parts of a 10% aqueous solution of polyvinyl alcohol is sprayed on it. The mixture is blended with 10 parts of white carbon to obtain coating type granule containing 10% of the compound.

FORMULATION EXAMPLE 8

Granules 10 parts of the compound (13), 30 parts of bentonite, 1 part of calcium lignosulfonate, 0.1 part of sodium laurylsulfate and 58.9 parts of kaolin clay are mixed. The mixture is kneaded with the addition of water, granulated through a screen of 7 mm. in mesh size and dried. Thus, granules containing 10% of the compound are prepared.

FORMULATION EXAMPLE 9

Water-surface-spreading oil based liquid 1 part of the compound (15), 10 parts of polyoxypropylene glycol monoether and 89 parts of kerosene are mixed to obtain a water-surface-spreading oil-based liquid.

What is claimed is:

1. A compound of the formula:

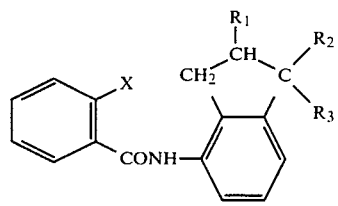

wherein X is a lower alkyl, nitro or trifluoromethyl group or a halogen atom, and $R_1$, $R_2$, and $R_3$, which are same or different, each represents a hydrogen atom or a lower alkyl group.

2. A fungicidal composition which comprises a fungicidal amount of a compound of the formula:

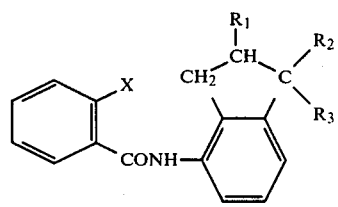

wherein X is a lower alkyl, nitro or trifluoromethyl group or a halogen atom, and $R_1$, $R_2$, and $R_3$, which are same or different, each represents a hydrogen atom or a lower alkyl group, and a carrier or diluent.

3. A compound according to claim 1 where x is methyl, nitro, trifluoromethyl, or halogen, $R_1$ is hydrogen or methyl, $R_2$ is hydrogen, methyl, or isopropyl, and $R_3$ is hydrogen, methyl, or ethyl.

4. A compound according to claim 3 where x is methyl or chlorine, $R_1$ is hydrogen, and $R_2$ is isopropyl.

5. A compound according to claim 1 where x is trifluoromethyl, $R_1$ is hydrogen, $R_2$ is methyl, and $R_3$ is hydrogen or methyl.

6. A process of preventing fungicidal attack comprising applying to the area to be protected a fungicidally effective amount of a compound according to claim 1.

7. A process of protecting plants from fungicidal attack comprising applying to the locus of the plant a fungicidally effective amount of a compound according to claim 1.

8. A compound according to claim 1 which is N-(1,1-dimethyl-4-indanyl)-o-trifluoromethylbenzamide.

9. A process of preventing fungicidal attack comprising applying to the area to be protected a fungicidally effective amount of the compound of claim 8.

10. A process of protecting plants from fungicidal attack comprising applying to the locus of the plant a fungicidally effective amount of the compound of claim 8.

* * * * *